United States Patent [19]

Toda et al.

[11] Patent Number: 5,395,977
[45] Date of Patent: Mar. 7, 1995

[54] PROCESS FOR PRODUCING OPTICAL ACTIVE 4-HYDROXY-2-CYCLOPENTENONE

[75] Inventors: Fumio Toda, Ehime; Yorihiko Inoue, Yao; Masayoshi Minai, Moriyama, all of Japan

[73] Assignee: Sumitomo Chemical Company, Ltd., Osaka, Japan

[21] Appl. No.: 31,182

[22] Filed: Mar. 12, 1993

[30] Foreign Application Priority Data

Mar. 13, 1992 [JP] Japan .................................. 4-055106

[51] Int. Cl.$^6$ ............................................. C07C 45/85
[52] U.S. Cl. ..................................... 568/366; 568/379
[58] Field of Search ................................ 568/366, 379

[56] References Cited

U.S. PATENT DOCUMENTS

| | | | |
|---|---|---|---|
| 4,683,341 | 7/1987 | Ishii et al. | 568/366 |
| 5,041,620 | 8/1991 | Toda et al. | 560/187 |

FOREIGN PATENT DOCUMENTS

| | | | |
|---|---|---|---|
| 63-83037 | 4/1988 | Japan | 568/366 |
| 63-179848 | 7/1988 | Japan | 568/366 |
| 4-66550 | 3/1992 | Japan | 560/187 |

OTHER PUBLICATIONS

Koichi Tanaka et al., "Efficient Optical Resolution of Some Key Compounds of Prostaaglandin Synthesis" Tetrahedron: Asymmetry, vol. 3, No. 4, 1992, Oxford, England, pp. 517–520.
Funio Toda et al., "Optical Resolution of Bicyclo (2.2.1) Heptanone, Bicyclo (2.2.2) Octanone, and Bicyclo (3.2.1) Octanone Derivatives by Inclusion Complexation with Optically Active Host Compounds", Journal of Organic Chemistry, vol. 56, 1991, Easton U.S., pp. 7332–7335.
Japanese publication No. 88-246713, Sumitomo Chemical Ind. K.K., Database WPI, Derwent Publications Ltd., London, England (abstract) (1988).
Summary of Lecture on "Asymmetric Recognition and Optical Resolution Utilizing Molecular Aggregtes" No. 63 1992, spring, fumio toda The Chemical Society of Japan.

*Primary Examiner*—James H. Reamer
*Attorney, Agent, or Firm*—Cushman, Darby & Cushman

[57] ABSTRACT

A process for producing optically active 4-hydroxy-2-cyclopentenone [1] which comprises reacting 4-hydroxy-2-cyclopentenone represented by the formula:

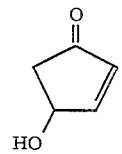

[4]

with an optically active propargyl alcohol derivative represented by the general formula:

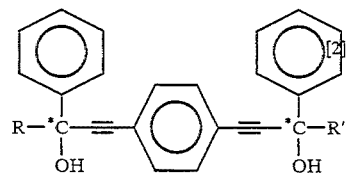

[2]

wherein R and R$^1$ each independently represent a halogenated phenyl group, an alkylphenyl group, or an alkyl group which may be substituted with one or more halogen atom(s), and * indicates an asymmetric carbon atom, to form an optically active complex [3] consisting essentially of optically active 4-hydroxy-2-cyclopentenone represented by the formula [1]

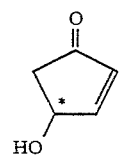

[1]

wherein * indicates an asymmetric carbon atom, and the optically active propargyl alcohol derivative [2], and then decomposing the optically active complex [3].

12 Claims, No Drawings

PROCESS FOR PRODUCING OPTICAL ACTIVE 4-HYDROXY-2-CYCLOPENTENONE

BACKGROUND OF THE INVENTION

1. Field of the Invention

The present invention relates to a process for producing optically active 4-hydroxy-2-cyclopentenone, to a precursor thereof and to a process for producing the precursor.

2. Description of the Related Art

Optically active 4-hydroxy-2-cyclopentenone is a compound useful as an intermediate for prostaglandins, anticholesterol agents, and the like. Known process for producing the compound include (1) one which comprises converting 4-hydroxy-2-cyclopentenone into its ester and hydrolyzing the ester with the aid of an enzyme (Japanese Patent Kokai (Laid-open) No. 63-000292), (2) one which comprises converting 4-hydroxy-2-cyclopentenone into its ester, reacting the ester with an optically active 1,6-diphenyl-4,4-hexadiyne-1,6-diol derivative to form a complex, separating the complex, then subjecting the complex to ligand exchange to obtain an ester of optically active 4-hydroxy-2-cyclopentenone and hydrolyzing the ester obtained (Japanese Patent Kokai (Laid-open) No. 63-179848) and (3) one which comprises reacting 4-hydroxy-2-cyclopentenone with an optically active lactone to obtain an ether compound, separating the ether compound into isomers and hydrolyzing the intended isomer (Japanese Patent Kokai (Laid-open) Nos. 57-159777, 60-199848 and 61-236742).

These processes, however, all have shortcomings in that it is indispensable for the processes once to convert 4-hydroxy-2-cyclopentenone into its derivative by esterification, etherification or such, and further they involve complicated separating operations, so that they are not satisfactory from the industrial viewpoint.

Recently, an attempt has been made to obtain from 4-hydroxy-2-cyclopentenone a corresponding optically active compound without protecting the hydroxyl group of the former (Japanese Patent Kokai (Laid-open) No. 4-66550). However, the results thus far obtained are not yet satisfactory.

In view of the situations, the present inventors have made extensive study on the process for producing optically active 4-hydroxy-2-cyclopentenone. As the result, it has been found that an optically active complex consisting essentially of optically active 4-hydroxy-2-cyclopentenone and an optically active propargyl alcohol derivative can be obtained in the form of crystal when racemic 4-hydroxy-2-cyclopentenone is reacted with the optically active propargyl alcohol derivative and further that optically active 4-hydroxy-2-cyclopentenone can be produced in a high optical yield and with an industrial advantage by decomposing the optically active complex obtained above without requiring to convert the racemic 4-hydroxy-2-cyclopentenone into its derivatives. The present invention has been accomplished on the basis of the above finding.

SUMMARY OF THE INVENTION

Thus, according to the present invention, there are provided a process for producing optically active 4-hydroxy-2-cyclopentenone [1] which comprises:
reacting 4-hydroxy-2-cyclopentenone represented by the formula [4]

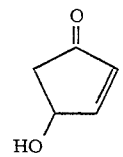

with an optically active propargyl alcohol derivative represented by the general formula [2]

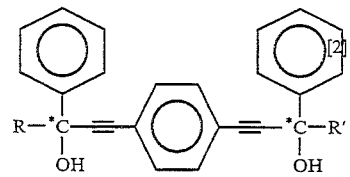

wherein R and $R^1$ each independently represent a halogenated phenyl group, an alkylphenyl group, or an alkyl group which may be substituted with one or more halogen atom(s), and * indicates an asymmetric carbon atom, to form an optically active complex [3] consisting essentially of optically active 4-hydroxy-2-cyclopentenone represented by the formula [1]

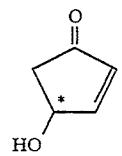

wherein * indicates an asymmetric carbon atom, and the optically active propargyl alcohol derivative [2], and then decomposing the optically active complex [3]; the optically active complex [3]; and a process for producing the optically active complex [3].

The present invention will be described in detail below.

The optically active complex [3] consisting essentially of optically active 4-hydroxy-2-cyclopentenone [1] and an optically active propargyl alcohol derivative [2] can be produced by reacting 4-hydroxy-2-cyclopentenone [4] with the optically active propargyl alcohol derivative [2].

In the reaction of forming the optically active complex, the 4-hydroxy-2-cyclopentenone [4] used is ordinarily a racemic mixture, but it may also be an optically active mixture which is rich in one of the optical isomers. The amount of 4-hydroxy-2-cyclopentenone [4] is usually at least 1 equivalent, preferably 2–5 equivalents, relative to the optically active propargyl alcohol derivative [2].

The optically active propargyl alcohol derivative [2] can be produced, for example, through the reaction scheme shown below.

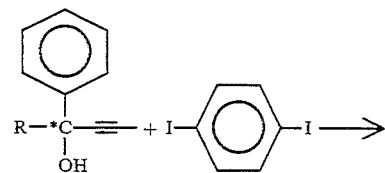

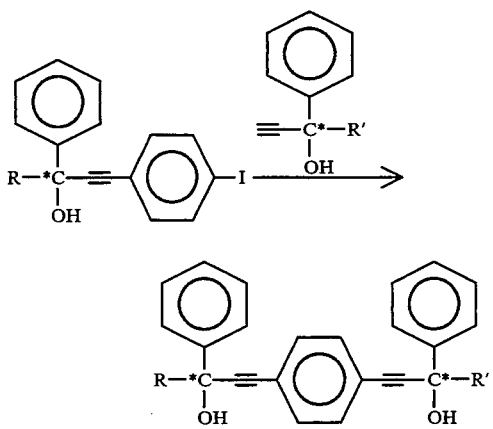

The substituents R and R[1] in the optically active propargyl alcohol derivative may be the same or different, but preferably the same with each other. Examples of the substituents R and R[1] include alkyl groups which may be substituted with one or more halogen atom(s), such as methyl, ethyl, propyl, butyl, chloromethyl, chloroethyl, bromopropyl, and fluorobutyl, halogenated phenyl groups such as chlorophenyl, fluorophenyl and bromophenyl, and alkylphenyl groups such as methylphenyl, ethylphenyl and propylphenyl. Alkyl groups commonly used are those of 1–5 carbon atoms, and alkylphenyl groups commonly used are those of 7–9 carbon atoms. Preferably used among these groups are chlorophenyl, fluorophenyl and bromophenyl, more preferably chlorophenyl. As specific examples of the derivative, mention may be made of (+) or (−)-1,4-bis[1-phenyl-1-(o-chloro-phenyl)- 1-hydroxypropynyl]-benzene, (+) or (−)-1,4-bis[1-phenyl-1-(o-bromophenyl)-1-hydroxypropynyl]benzene, (+) or (−)-1,4-bis[1-phenyl-1-(o-fluorophenyl)-1-hydroxypropynyl]-benzene, (+) or (−)-1,4-bis[1-phenyl-1-(p-chlorophenyl)-1-hydroxypropynyl]benzene, (+) or (−)-1,4-bis[1-phenyl-1-(o-methylphenyl)-1-hydroxypropynyl]-benzene, (+) or (−)-1,4-bis[1-phenyl-1-(o-ethylphenyl)-1-hydroxypropynyl]benzene, (+) or (−)-1,4-bis[1-phenyl-1-(p-methylphenyl)-1-hydroxypropynyl]-benzene, (+) or (−)-1,4-bis[1-phenyl-1-(p-propylphenyl)-1-hydroxypropynyl]benzene, (+) or (−)-1,4-bis[1-phenyl-1-(2-chloroethyl)-1-hydroxypropynyl]benzene, (+) or (−)-1,4-bis[1-phenyl-1-(4-chlorobutyl)-1-hydroxypropynyl]benzene, (+) or (−)-1,4-bis[1-phenyl-1-propyl-1-hydroxypropynyl]benzene, (+) or (−)-1,4-bis[1-phenyl-1-methyl-1-hydroxypropynyl]benzene, (+) or (−)-[1-phenyl-1-(o-chlorophenyl)-1-hydroxypropynyl]-4-[1-phenyl-1-(o-bromophenyl)-1-hydroxypropynyl]benzene, (+) or (−)-1-[1-phenyl-1-(o-chlorophenyl)-1-hydroxypropynyl]-4-[1-phenyl-1-(o-methylphenyl)-1-hydroxypropynyl]benzene, and (+) or (−)-1-[1-phenyl-1-(o-bromophenyl)-1-hydroxypropynyl]-4-[1-phenyl-1-(o-ethylphenyl)-1-hydroxypropynyl]benzene.

Though the use of a solvent is not essential in the reaction of forming the optically active complex [3], the reaction is usually conducted in the presence of a solvent. Example of solvents which may be used include alcohols such as methanol, ethanol, propanol, butanol and cyclopentanol; hydrocarbons, e.g., aromatic hydrocarbons such as benzene, toluene, xylene, and ethylbenzene, aliphatic hydrocarbons such as hexane, heptane, octane, ligroin and petroleum ether, and acicyclic hydrocarbons such as cyclopentane, cyclohexane, and cycloheptane; aliphatic halogenated hydrocarbons such as carbon tetrachloride, chloroform, dichloromethane and dichloroethane, aromatic halogenated hydrocarbons such as chlorobenzene and dichlorobenzene; ethers such as ethyl ether, methyl butyl ether, esters such as ethyl acetate, and polar solvents such as acetonitrile. These solvents may be used each alone or as a mixture thereof. Preferred among them are alcohols and hydrocarbons. Preferred among alcohols are alcohols of 1–6 carbon atoms. Particularly preferred are benzene, toluene and ethanol. Most preferred is ethanol.

The reaction temperature may be selected as derived from the range of from −20° C. to the boiling point of the solvent used, but is usually in the range of from 0° C. to 80° C. The contact of 4-hydroxy-2-cyclopentenone represented by the formula [4] with the optically active propargyl alcohol derivative represented by the formula [2] results in the formation of the crystal of optically active complex [3]. Crystallization of the optically active complex [3] can be promoted, if necessary and desired, by such means as addition of a seed crystal, cooling of the reaction mixture at the time of crystallization, or addition of a solvent, particularly an aliphatic hydrocarbon such as hexane and heptane, to the reaction mixture.

After completion of the reaction, the reaction mixture is subjected, for example, to filtration and washing to obtain the optically active complex [3] in the form of crystal, which may be further purified as occasion demands.

When an alcohol is used as the solvent in the above reaction, an optically active complex [3] consisting essentially of a (+) optically active propargyl alcohol derivative [2] and (+) optically active 4-hydroxy-2-cyclopentenone [1] is formed from the (+) compound [2] and 4-hydroxy-2-cyclopentenone [4], and a complex [3] consisting essentially of the (−) compound [2] and the (−) compound [1] is formed from the (−) compound [2] and the compound [4]. In these cases, the crystals of the optically active complex [3] sometimes, depending on reaction conditions, contain the solvent incorporated therein. In such a case, the crystals may be used as such for the succeeding decomposition step. When a hydrocarbon is used as the solvent in the reaction, a complex [3] consisting essentially of the (+) compound [2] and the (−) compound [1] is formed from the (+) compound [2] and the compound [4], and a complex [3] consisting essentially of the (−) compound [2] and the (+) compound [1] is formed from the (−) compound [2] and the compound [4].

Thus, even when one of the optical isomers of the optically active propargyl alcohol derivative [2] is used, the isomer of 4-hydroxy-2-cyclopentenone which constitutes the complex can be selectively prepared as desired by proper choice of the solvent. On the other hand, the filtrate obtained after the crystals of the optical active complex [3] have been filtered off can be recycled for use, for example, after converting the filtrate into a racemic mixture. Further, for example, after the reaction has been completed by using an alcohol and the optically active complex [3] has been separated and collected as crystals by filtration, when the filtrate is concentrated, then the optically active propargyl alcohol derivative [2] is supplemented thereto if necessary, and the concentrated filtrate is treated with a hydrocarbon, an optically active complex [3] containing an optically active 4-hydroxy-2-cyclopentenone which is an optical isomer reverse to the optically active 4-hydroxy-2-cyclopentenone obtained before can be obtained as crystals.

The intended optically active 4-hydroxy-2-cyclopentenone [1] is obtained by decomposing the optically active complex [3] consisting essentially of the optically active propargyl alcohol derivative [2] and the optically active 4-hydroxy-2-cyclopentenone [1] obtained as described above.

The decomposition can be easily effected by such means as melting or dissolution into a solvent. The decomposition of the optically active complex [3] and the separation of the optically active 4-hydroxy-2-cyclopentenone formed can be performed, for example, by the following methods. Method (3) is preferred from the industrial point of view.

(1) Distillation
(2) Chromatography
(3) Action by guest molecule.

First, method (1) is described below.

By melting and distilling the optically active complex [3] under normal or reduced pressure, optically active 4-hydroxy-2-cyclopentenone [1] can be distilled out. The distillation is ordinarily conducted under reduced pressure, usually at 0.1–30 mmHg. The optically active propargyl alcohol derivative [2] can be recovered and recycled.

Secondly, method (2) is described below.

The optically active complex [3] is dissolved in the same solvent as that used in the complex formation and subjected to chromatography, for example column chromatography or the like, whereby optically active 4-hydroxy-2-cyclopentenone [1] can be obtained.

The developing solvent may be, for example, toluene, ethyl acetate and chloroform, used each alone or as a mixture. The optically active propargyl alcohol derivative [2] can be recovered and recycled.

Method (3) is then described below.

Optically active 4-hydroxy-2-cyclopentenone [1] can be obtained by acting guest molecules on the optically active complex [3].

In this method, the optically active complex [3] and guest molecules are mixed, and a complex consisting essentially of the optically active propargyl alcohol derivative [2] and the guest molecules is precipitated as crystals and removed, whereby optically active 4-hydroxy-2-cyclopentenone [1] is obtained as the filtrate. This method can be accomplished in various manners, for example, through the following ways.

(1) The optically active complex [3] and the guest molecules are mixed with a solvent and made into a uniform solution with or without heating. A complex consisting essentially of the guest molecules and the optically active propargyl alcohol derivative [2] is then precipitated therefrom with or without cooling.

(2) The optically active complex [3] and an excess amount of the guest molecules are mixed and heated to form a uniform solution, which is then cooled to precipitate a complex consisting essentially of the guest molecule and the optically active propargyl alcohol derivative [2].

The solvent herein refers to those similar to the solvents used in the preparation of the optically active complex [3] described above, and the same solvent as that used above may be employed also in this method.

(3) The optically active complex [3] and the guest molecules are mixed to form a uniform solution and then a solvent is added thereto to precipitate a complex consisting essentially of the guest molecule and the optically active propargyl alcohol derivative [2].

Examples of the compound which may be used as guest molecules in the above-mentioned reaction include ketones, such as methyl ethyl ketone, diethyl ketone, acetone, cyclopentanone and cyclohexanone, cyclic ethers such as tetrahydrofuran, dioxane, and tetrahydropyran, aliphatic amines such as dimethylamine, diethylamine and triethylamine, aromatic amines such as aniline, toluidine, xylidine and anisidine, aromatic aldehydes such as benzaldehyde, salicylaldehyde and anisaldehyde, aliphatic sulfoxide such as dimethyl sulfoxide and diethyl sulfoxide, and formamide such as N,N-dimethylformamide. They are used in an amount of usually at least 1 equivalent, preferably 2–10 equivalents, relative to the optically active complex [3].

The reaction temperature may be selected as desired from the range of from $-20°$ C. to the boiling point of the solvent or the guest molecule used. It is usually in the range of $-10°$ to $100°$ C.

After completion of the reaction, the precipitated complex consisting essentially of the guest molecules and the optically active propargyl alcohol derivative [2] is removed by filtration, and then optically active 4-hydroxy-2-cyclopentenone [1] is obtained, for example, by concentrating the filtrate, which may be further purified, if necessary and desired, by chromatography, distillation, and the like.

The complex consisting essentially of the guest molecules and the optically active propargyl alcohol derivative [2], collected above by filtration, may be subjected, for example, to heating under reduced pressure or column chromatography, to recover and recycle as the optically active propargyl alcohol derivative [2].

According to the present invention, optically active 4-hydroxy-2-cyclopentenone [1] can be obtained in a high optical yield. According to the present invention, further, the intended compound [1] can be obtained by using 4-hydroxy-2-cyclopentenone [4] directly without requiring to convert the compound [4] into its derivative, and hence with more simple and efficient operations than in the prior processes. Thus, the present process is of great industrial advantage.

DESCRIPTION OF THE PREFERRED EMBODIMENTS

The present invention will be described in more detail below with reference to Examples, but the invention is in no way limited thereto.

EXAMPLE 1

In a four-necked flask equipped with a stirrer, thermometer and cooling tube were placed 2.79 g of (−)-1,4-bis[1-phenyl-1-(o-chlorophenyl)-1-hydroxypropynyl]benzene, 1.96 g of 4-hydroxy-2-cyclopentenone and 215 ml of ethanol and made to dissolve into a uniform solution at 75°–80° C. The solution was kept at the same temperature for about 1 hour and then gradually cooled down to room temperature. The white prism-like crystals thus precipitated were collected by filtration to obtain 2.11 g of an optically active complex consisting essentially of (−)-1,4-bis[1-phenyl-1-(o-chlorophenyl)-1-hydroxypropynyl]benzene, (−)-4-hydroxy-2-cyclopentenone and ethanol in a ratio of 1:1:1, in the form of crystals.

m.p. 92°–93° C., $[\alpha]_D^{20}$ −57.0° (c=4.0, CHCl$_3$), optical purity 98.0% e.e. (as determined by HPLC)

¹H-NMR (270 MHz, CDCl₃) δ(ppm) 1.21(t, 3H)(Et), 2.2–2.3(dd, 2H)(−S), 2.7–2.8(dd, 1H)(−S), 3.3(S, 2H)(−P), 3.6–3.7(dd, 2H)(Et), 6.2(d, 1H)(−S), 7.2–7.9(m, 23H)(−P, −S)

(Herein, −S, −P and Et refer to peaks respectively originating from (−)-4-hydroxy-2-cyclopentenone, (−)-1,4-bis[1-phenyl-1-(o-chlorophenyl)-1-hydroxypropynyl]benzene and ethanol.)

EXAMPLE 2

The same procedures as in Example 1 were followed except for using (+)-1,4-bis[1-phenyl-1-(o-clorophenyl)-1-hydroxypropynyl]benzene to obtain an optically active complex consisting essentially of (+)-1,4-bis[1-phenyl-1-(o-chlorophenyl)-1-hydroxypropynyl]benzene, (+)-4-hydroxy-2-cyclopentenone and ethanol in a ratio of 1:1:1.

$[\alpha]_D^{20}$ +57.0° (c=4, CHCl₃) optical purity 98% e.e.

EXAMPLE 3

In a four-necked flask equipped with a stirrer, thermometer and cooling tube were placed 11.18 g of (−)-1,4-bis[1-phenyl-1-(o-chlorophenyl)-1-hydroxypropynyl]benzene, 7.84 g of 4-hydroxy-2-cyclopentenone and 20 ml of toluene and made into a solution at room temperature. The solution was then kept at the same temperature for 6 hours, and the prism-like crystals thus precipitated were collected by filtration to obtain 10.9 g of an optically active complex consisting essentially of (−)-1,4-bis[1-phenyl-1-(o-chlorophenyl)-1-hydroxypropynyl]benzene and (+)-4-hydroxy-2-cyclopentenone in a ratio of 1:2, in the form of crystals. The crystals were further recrystallized from toluene three times to obtain 2.6 g of an optically active complex consisting essentially of (−)-1,4-bis[1-phenyl-1-(o-chlorophenyl)-1-hydroxypropynyl]benzene and (+)-4-hydroxy-2-cyclopentenone in a ratio of 1:2.

m.p. 91°–94° C., $[\alpha]_D^{20}$ −20.3° (c=4.0, CHCl₃), optical purity 77.0% e.e. (as determined by HPLC).

¹H-NMR (270 MHz, CDCl₃), δ(ppm) 2.2–2.3(dd, 4H)(+S), 2.7–2.8(dd, 2H)(+S), 3.3(3, 2H)(−P), 6.2(d, 2H)(+S), 7.2–7.9(m, 24H)(−P, +S)

(Herein, +S and −P refer to peaks respectively originating from (+)-4-hydroxy-2-cyclopentenone and (−)-1,4-bis[1-phenyl-1-(o-chlorophenyl)-1-hydroxypropynyl]benzene.)

EXAMPLE 4

The same procedures of reaction, after-treatment and recrystallization as those in Example 3 are followed except for using (+)-1,4-bis[1-phenyl-1-(o-chlorophenyl)-1-hydroxypropynyl]benzene in place of (−)-1,4-bis[1-phenyl-1-(o-chlorophenyl)-1-hydroxypropynyl]benzene to obtain an optically active complex consisting essentially of (+)-1,4-bis[1-phenyl-1-(o-chlorophenyl)-1-hydroxypropynyl]benzene and (−)-4-hydroxy-2-cyclopentenone in a ratio of 1:2.

EXAMPLE 5

(1) A mixture of 4.2 g of an optically active complex consisting essentially of (−)-1,4-bis[1-phenyl-1-(o-chlorophenyl)-1-hydroxypropynyl]benzene, (−)-4-hydroxy-2-cyclopentenone and ethanol in a ratio of 1:1:1 obtained in the same manner as in Example 1 and 4 g of acetone was heated under reflux for 3 hours. Thereafter, 20 ml of hexane was added, the resulting mixture was cooled down to 10° C. and kept at 0°–10° C. for 1 hour. The white crystals thus precipitated were filtered off to obtain 3.86 g of a complex consisting essentially of (−)-1,4-bis[1-phenyl-1-(o-chlorophenyl)-1-hydroxypropynyl] benzene and acetone in a ratio of 1:2 as crystals, and a filtrate. The crystals were kept at a pressure of 5–10 mmHg and a temperature of 70°–80° C. to expel acetone, whereby 3.1 g of (−)-1,4-bis[1-phenyl-1-(o-chlorophenyl)-1-hydroxypropynyl]benzene was obtained.

m.p. 122°–125° C., $[\alpha]_D^{20}$ −61.0° (c=1.0, MeOH)

(2) On the other hand, the filtrate obtained in (1) above was concentrated, and the concentration residue was purified by column chromatography to obtain 0.58 g of (−)-4-hydroxy-2-cyclopentenone.

$[\alpha]_d^{20}$ −96° (c=4, CHCl₃), optical purity 98.0% e.e. (as determined by HPLC)

EXAMPLE 6

The same procedures as in (1) of Example 5 were followed to obtain a filtrate, which was then concentrated to give a concentration residue. Then 0.78 g of the concentration residue was distilled under reduced pressure to obtain 0.52 g of (−)-4-hydroxy-2-cyclopentenone.

$[\alpha]_D^{20}$ −92° (c=4, CHCl₃), optical purity 97.5% e.e. (as determined by HPLC)

EXAMPLE 7

The filtrate obtained in Example 3 was concentrated under reduced pressure. To the resulting residue were added 30 ml of ethanol and 11.18 g of (−)-1,4-bis[1-phenyl-1-(o-chlorophenyl)-1-hydroxypropynyl]benzene, and the mixture was made into a uniform solution at 75°–80° C. The solution was then kept at the same temperature for about 1 hour and cooled gradually down to room temperature. The prism-like white crystals thus precipitated were collected by filtration to obtain 8.3 g of an optical active complex consisting essentially of (−)-1,4-bis[1-phenyl-1-(o-chlorophenyl)-1-hydroxypropynyl]benzene, (−)-4-hydroxy-2-cyclopentenone and ethanol in a ratio of 1:1:1.

$[\alpha]_D^{20}$ −56.8° (c=4, CHCl₃), optical purity 97.8% e.e. (as determined by HPLC)

EXAMPLE 8

The filtrate obtained in Example 2 is concentrated under reduced pressure. To the resulting residue are added toluene and (+)-1,4-bis[1-phenyl-1-(o-chlorophenyl)-1-hydroxypropynyl]benzene, the mixture is made into solution at room temperature and kept at the same temperature. The prism-like white crystals thus precipitated are collected by filtration to obtain a complex consisting essentially of (+)-1,4-bis[1-phenyl-1-(o-chlorophenyl)-1-hydroxypyropynyl]benzene and (−)-4-hydroxy-2-cyclopentenone in a ratio of 1:2.

EXAMPLE 9

Two (2) grams of an optical active complex consisting essentially of (−)-1,4-bis[1-phenyl-1-(o-chlorophenyl)- 1-hydroxypropynyl]benzene, (−)-4-hydroxy-2-cyclopentenone and ethanol in a ratio of 1:1:1 obtained in the same manner as in Example 1 was subjected to column chromatography using a 10:2 liquid mixture of toluene and ethyl acetate as the developing solvent to obtain 0.25 g of (−)-4-hydroxy-2-cyclopentenone.

$[\alpha]_D^{20}$ −96.5° (c=4, CHCl₃), optical purity 98.0% e.e. (as determined by HPLC).

EXAMPLE 10

Eight (8) grams of the optical active complex consisting essentially of (−)-1,4-bis[1-phenyl-1-(o-chlorophenyl)-1-hydroxypropynyl]benzene, (−)-4-hydroxy-2-cyclopentenone and ethanol in a ratio of 1:1:1 obtained in Example 7 was distilled with heating under reduced pressure to obtain 1.0 g of (−)-4-hydroxy-2-cyclopentenone.

b.p. 110° C./4 mmHg, $[\alpha]_D^{20}$ −96.0° (c=4, CHCl$_3$)

PREPARATION EXAMPLE 1

In a 1000-ml egg-plant type flask were mixed 53.5 g of (−)-1-phenyl-1-(o-chlorophenyl)-2-propyn-1-ol ($[\alpha]_D^{20}$=−138°), 26.0 g of p-dibromobenzene and 280 ml of triethylamine, then 0.10 g of PdCl$_2$(PPh$_3$)$_2$, 0.10 g of CuI and 0.52 g of PPh$_3$ were added thereto, a Dimroth condenser was connected to the flask, and the reaction mixture was allowed to reflux for about 4 hours. After being cooled by standing, the reaction mixture was diluted by addition of 300 ml of ether, the salt of triethylamine and hydrogen bromide formed was removed by filtration, and the salt was washed with ether. The filtrate and the washing were washed with water and dilute hydrochloric acid and further with aqueous sodium bicarbonate solution and saturated aqueous sodium chloride solution. The organic layer was dried with anhydrous sodium sulfate and then concentrated. Acetone was added to the concentration residue and the mixture was allowed to stand to obtain as crystals a complex consisting essentially of (−)-1,4-bis[1-phenyl-1-(o-chlorophenyl)-1-hydroxypropynyl]-benzene and acetone. The complex was recrystallized from acetone several times and then dried in a glass tube oven to obtain 49.3 g of (−)-1,4-bis[1-phenyl-1-(o-chlorophenyl)-1-hydroxypropynyl]benzene.

m.p. 72°-83° C., $[\alpha]_D^{20}$=−62.6° (c=1.13, MeOH)

PREPARATION EXAMPLE 2

The same procedures of reaction and after-treatment as in Preparation Example 1 are followed except for using (+)-1-phenyl-1-(o-chlorophenyl)-2-propyn-1-ol, to obtain (−)-1,4-bis[1-phenyl-1-(o-chlorophenyl)-1-hydroxypropynyl]benzene.

What is claimed is:

1. A process for producing optically active 4-hydroxy-2-cyclopentenone (1) which comprises:

reacting 4-hydroxy-2-cyclopentenone represented by the formula:

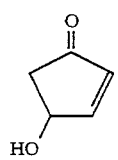

[4]

with an optically active propargyl alcohol derivative represented by the general formula:

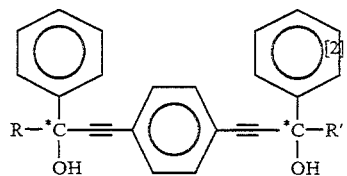

wherein R and R' each independently represent a halogenated phenyl group, an alkylphenyl group, or an alkyl group which may be substituted by one or more halogen atom(s), and * indicates an asymmetric carbon atom, to form an optically active complex (3) consisting essentially of optically active 4-hydroxy-2-cyclopentenone represented by the formula:

[1]

wherein * indicates an asymmetric carbon atom, and the optically active propargyl alcohol derivative (2); and then decomposing the complex (3).

2. A process for producing optically active 4-hydroxy-2-cyclopentenone according to claim 1, wherein the substituents R and R' are each chlorophenyl.

3. A process for producing optically active 4-hydroxy-2-cyclopentenone according to claim 1, wherein the reaction is conducted in an alcohol.

4. A process for producing optically active 4-hydroxy-2-cyclopentenone according to claim 1, wherein the substituents R and R' are each chlorophenyl and the reaction is conducted in an alcohol.

5. A process for producing optically active 4-hydroxy-2-cyclopentenone (1) which comprises:

reacting 4-hydroxy-2-cyclopentenone represented by the formula:

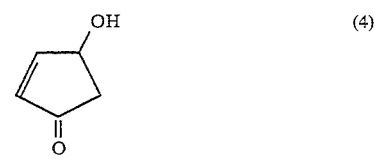

(4)

with an optically active propargyl alcohol derivative represented by the general formula:

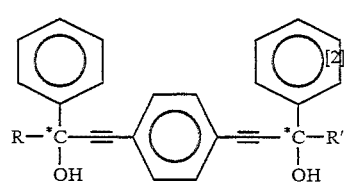

wherein R and R' each independently represent a halogenated phenyl group, an alkylphenyl group, or an alkyl group which may be substituted by one or more halogen atom(s), and * indicates an asymmetric carbon atom, to form an optically active complex (3) consisting essentially of optically active 4-hydroxy-2-cyclopentenone represented by the formula:

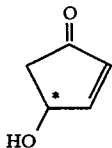

[1]

wherein * indicates an asymmetric carbon atom, and the optically active propargyl alcohol derivative (2), wherein the reaction is conducted in the presence of a solvent and at a temperature in a range of from −20° C. to up to the boiling point of the solvent; and then decomposing the complex (3).

6. An optically active complex (3) consisting essentially of optically active 4-hydroxy-2-cyclopentenone represented by the formula (1):

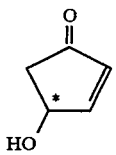

[1]

wherein * indicates an asymmetric carbon atom, and an optically active propargyl alcohol derivative (2) which is selected from the group consisting of (+) or (−)-1,4-bis(1-phenyl-1-(o-chlorophenyl)-1-hydroxypropynyl) benzene, (+) or (−)-1,4-bis(1-phenyl-1-(o-bromophenyl)-1-hydroxypropynyl) benzene, (+) or (−)-1,4-bis(1-phenyl-1-(o-fluorophenyl)-1-hydroxypropynyl) benzene, (+) or (−)-1,4-bis(1-phenyl-1-(p-chlorophenyl)-1-hydroxypropynyl) benzene, (+) or (−)-1,4bis(1-phenyl-1-(o-methylphenyl)-1-hydroxypropynyl) benzene, (+) or (−)-1,4-bis(1-phenyl-1-(o-ethylphenyl)-1-hydroxypropynyl) benzene, (+) or (−)-1,4-bis(1-phenyl-1-(p-methylphenyl)-1-hydroxypropynyl) benzene, (+) or (−)-1,4-bis(1-phenyl-1-(p-propylphenyl)-1-hydroxypropynyl) benzene, (+) or (−)-1,4-bis(1-phenyl-1-(2-chloroethyl)-1-hydroxypropynyl) benzene, (+) or (−)-1,4bis(1-phenyl-1-(4-chlorobutyl)-1-hydroxypropynyl) benzene, (+) or (−)-1,4-bis(1-phenyl-1-propyl-1-hydroxypropynyl) benzene, (+) or (−)-1,4-bis(1-phenyl-1-methyl-1-hydroxypropynyl) benzene, (+) or (−)-(1-phenyl-1-(o-chlorophenyl)-1-hydroxypropynyl)-4-(1-phenyl-1-(o-bromophenyl)-1-hydroxypropynyl) benzene, (+) or (−)-1-(1phenyl-1-(o-chlorophenyl)-1-hydroxypropynyl)-4-(1phenyl-1-(o-methylphenyl)-1-hydroxypropynyl) benzene, and (+) or (−)-1-(1-phenyl-1-(o-bromophenyl)-1-hydroxypropynyl)-4-(1-phenyl-1-(o-ethylphenyl)-1-hydroxypropynyl) benzene.

7. An optically active complex (3) according to claim 6, wherein the complex consists essentially of a (+) optically active substance (1) and a (+) optically active substance (2).

8. An optically active complex (3) according to claim 6, wherein the complex consists essentially of a (+) optically active substance (1) and a (−) optically active substance (2).

9. A process for producing an optically active complex (3) consisting essentially of optically active 4-hydroxy-2-cyclopentenone (1) and an optically active propargyl alcohol derivative (2) which comprises reacting 4-hydroxy-2-cyclopentenone (4) with an optically active propargyl alcohol derivative.

10. A process for producing optically active complex (3) according to claim 9, wherein the optically active propargyl alcohol derivative is represented by the formula:

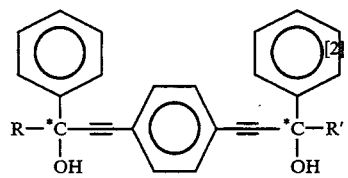

wherein the substituents R and R' are each chlorophenyl, and * represents an asymmetric carbon atom.

11. A process according to claim 9, wherein the reaction is conducted in an alcohol.

12. A process for producing optically active complex (3) according to claim 10, wherein the reaction is conducted in an alcohol.

* * * * *